(12) United States Patent
Remes et al.

(10) Patent No.: US 10,342,440 B2
(45) Date of Patent: Jul. 9, 2019

(54) CONTROL MODULE AND AN ARRANGEMENT FOR MEASURING A BIOSIGNAL

(71) Applicant: Mega Elektroniikka Oy, Kuopio (FI)

(72) Inventors: Arto Remes, Kuopio (FI); Aki Tiihonen, Kuopio (FI); Sami Hynynen, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 118 days.

(21) Appl. No.: 14/424,505

(22) PCT Filed: Aug. 9, 2013

(86) PCT No.: PCT/FI2013/050790
§ 371 (c)(1),
(2) Date: Feb. 27, 2015

(87) PCT Pub. No.: WO2014/033360
PCT Pub. Date: Mar. 6, 2014

(65) Prior Publication Data
US 2015/0208932 A1     Jul. 30, 2015

(30) Foreign Application Priority Data
Aug. 28, 2012  (FI) ........................... 20125887

(51) Int. Cl.
*A61B 5/042*     (2006.01)
*A61B 5/024*     (2006.01)
(Continued)

(52) U.S. Cl.
CPC ........ *A61B 5/02405* (2013.01); *A61B 5/0006* (2013.01); *A61B 5/02438* (2013.01);
(Continued)

(58) Field of Classification Search
CPC . A61B 5/0004; A61B 5/02405; A61B 5/6803; A61B 5/0533; A61B 5/0243
(Continued)

(56) References Cited

U.S. PATENT DOCUMENTS 4,305,402 A * 12/1981 Katims ................ A61B 5/0484
                                                     128/905
4,966,164 A * 10/1990 Colsen ................. A61H 39/002
                                                     128/907
(Continued)

FOREIGN PATENT DOCUMENTS

CN      201379564 Y     1/2010
CN      101664308 A     3/2010
(Continued)

OTHER PUBLICATIONS

First Notification of Office Action (Translation), Chinese patent application No. 201380056082.5, dated May 4, 2016.
(Continued)

*Primary Examiner* — Alyssa M Alter
(74) *Attorney, Agent, or Firm* — Marshall, Gerstein & Borun LLP

(57) ABSTRACT

The present disclosure discloses an arrangement for measuring a biosignal. The arrangement has a sensor module and a control module. The sensor module has structure for sensing at least one biosignal and a first connector for interfacing with the control module. The control module has a first counterpart connector connected to the first connector of the sensor module, structure for processing biosignal data sensed with the sensor module, a storage memory for storing processed bio signal data, a rechargeable battery for providing operating power for the control module, structure for wirelessly transmitting the processed biosignal data to a computing device, such as a PC, a tablet PC or a smart
(Continued)

phone, for post-processing, and a second connector for interfacing with a second electrode.

17 Claims, 3 Drawing Sheets

(51) Int. Cl.
*A61B 5/00* (2006.01)
*A61B 5/0488* (2006.01)
*A61B 5/0402* (2006.01)
*A61B 5/0476* (2006.01)
*A61B 5/053* (2006.01)
*A61B 5/0408* (2006.01)
*A61B 5/0478* (2006.01)

(52) U.S. Cl.
CPC .......... *A61B 5/0402* (2013.01); *A61B 5/0476* (2013.01); *A61B 5/0488* (2013.01); *A61B 5/0533* (2013.01); *A61B 5/0535* (2013.01); *A61B 5/6803* (2013.01); *A61B 5/02416* (2013.01); *A61B 5/0408* (2013.01); *A61B 5/0478* (2013.01); *A61B 5/6816* (2013.01); *A61B 5/6824* (2013.01); *A61B 5/7405* (2013.01); *A61B 2560/045* (2013.01); *A61B 2562/227* (2013.01)

(58) Field of Classification Search
USPC .................................... 607/60; 600/300, 301
See application file for complete search history.

(56) References Cited

U.S. PATENT DOCUMENTS

| | | | |
|---|---|---|---|
| 6,409,675 B1 * | 6/2002 | Turcott | A61B 5/0002 600/504 |
| 2003/0181798 A1 | 9/2003 | Al-Ali | |
| 2007/0177298 A1 | 8/2007 | Jaatinen et al. | |
| 2009/0018456 A1 * | 1/2009 | Hung | A61B 5/02438 600/509 |
| 2010/0145236 A1 | 6/2010 | Greenberg et al. | |
| 2010/0274109 A1 | 10/2010 | Hu et al. | |
| 2011/0201382 A1 | 8/2011 | Hsiao | |
| 2012/0156933 A1 | 6/2012 | Kreger et al. | |

FOREIGN PATENT DOCUMENTS

| | | |
|---|---|---|
| GB | 2463784 A | 3/2010 |
| WO | WO-2004/093676 A1 | 11/2004 |
| WO | WO-2012/112891 A1 | 8/2012 |

OTHER PUBLICATIONS

Extended European Search Report, European patent application No. 13832726.7, dated Apr. 1, 2016.
International Search Report and Written Opinion, International Application No. PCT/FI2013/050790, dated Nov. 29, 2013.
International Preliminary Report on Patentability, International Application No. PCT/FI2013/050790, dated Mar. 3, 2015.

* cited by examiner

CONTROL MODULE AND AN ARRANGEMENT FOR MEASURING A BIOSIGNAL

CROSS-REFERENCE TO RELATED APPLICATION

This is the U.S. national phase of International Application No. PCT/FI2013/050790, filed Aug. 9, 2013, which claims the benefit of Finnish Patent Application No. 20125887, filed Aug. 28, 2012.

FIELD OF THE INVENTION

The present invention relates to measuring biosignals.

BACKGROUND INFORMATION

Measurement and interpretation of biosignals can be utilized in many different applications. A biosignal is in this context a signal representing a measurable variable of a living being. Examples of biosignals are body movement and temperature, heart rate variability (HRV), electrocardiogram (ECG), electromyogram (EMG) and electroencephalogram (EEG). The term biosignal is not, however, limited to these examples in this disclosure. It may be any a measurable variable of a living being.

In order to measure a biosignal, such as the heart rate variability (HRV), the person whose biosignal is measured may be equipped with a pair of electrodes attached to the chest. The electrodes may be secured to their positions by using a band stretching around the chest.

Wiring of the electrodes and the chest band may be very restrictive for the person. The wiring may be restrictive for mobility, and the chest band may restrict breathing, particularly in sports.

BRIEF DISCLOSURE

An object of the present invention is to provide an arrangement so as to alleviate the above disadvantages. The objects of the invention are achieved by an arrangement, and a control module, a sensor module and an electrode for the arrangement which are characterized by what is stated in the independent claims. The preferred embodiments of the invention are disclosed in the dependent claims.

The disclosed arrangement comprises a sensor module attached to a control module. The sensor module is capable of sensing at least one biosignal. The sensor module may, for example, be used to sense heart rate variability (HRV). The sensor module may be attached to the chest of the user, i.e. the individual wearing the arrangement. Alternatively, the sensing module can be implemented in the form of an armband which senses HRV with the aid of an electrode connected to one ear of the user.

The control module processes the biosignal/s sensed with the sensor module. The control module can store processed biosignal data to a storage memory on the control module and/or wirelessly transmit the biosignal data to a computing device, such as a PC, a tablet, a smart phone, etc. The computing device can then be used for post-processing the biosignal data and/or visualising it on a user interface.

The sensor module and the control module may be connected to each other through a connector pair forming a connector interface. The biosignal data can be transferred from the sensor module to the control module through the interface.

The connectors of the connector interface can be detachable. In this manner, the control module can be detached from the sensor module, and attached to another sensor module. The control module comprises a rechargeable battery. The rechargeable battery can also be used to power the attached sensor module through the connector interface. When the connector interface is a standard connector interface, such as USB, the control module can also easily be connected to a computing device for post-processing and/or visualisation. Further, the computing device can be used for recharging the battery of the control unit through the connector interface.

The control module may be connected to a sensor module which comprises an armband having a first electrode placed in the surface of the armband facing the user's skin. The control module may also comprise a connector for a second electrode. The electrode may, for example, be adapted to be attached to the user's ear or arm.

The modular structure having the detachable connector interface between the sensor module and the control module of the disclosed arrangement allows a cost-effective way for sensing biosignals in more than one manner. The modular structure also allows maintaining personal safety of the user. The biosignal data can be transferred to the computing device, and the control module can be recharged without a galvanic connection to the user. This also allows the use of permanent electrodes.

By using the disclosed arrangement with the ear electrode and the electrode in the armband, HRV can be sensed without any need for restrictive electrode wiring or chest band.

BRIEF DESCRIPTION OF THE DRAWINGS

In the following the invention will be described in greater detail by means of preferred embodiments with reference to the attached drawings, in which.

DETAILED DISCLOSURE

Figure 1A:
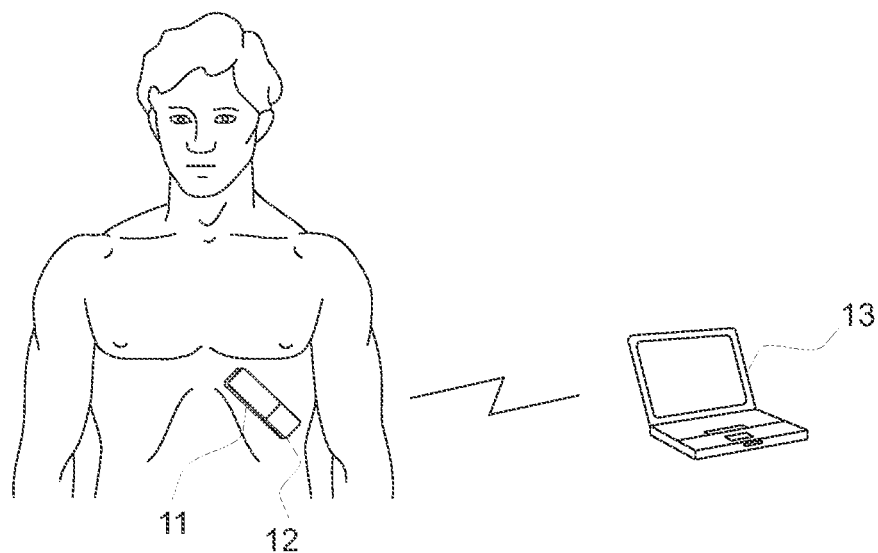
FIGS. 1a and 1b illustrate an embodiment of the disclosed arrangement.

The present disclosure discloses an arrangement for measuring a biosignal. The present disclosure further discloses a sensor module, a control module, and an electrode for the arrangement.

The disclosed arrangement comprises the sensor module connected to the control module. The sensor module comprises means for sensing at least one biosignal. The sensor module may, for example, be adapted for sensing heart rate variability (HRV), electrocardiogram (ECG), electromyogram (EMG) or electroencephalogram (EEG).

The sensor module further comprises a first connector for interfacing with a control module while the control module comprises a first counterpart connector attached to the first connector. The biosignal data can be transferred from the sensor module to the control module through the interface formed by the first connector connected to the first counterpart connector.

The first connector and the first counterpart connector can be adapted such that the connection between the sensor module and the control module can be disconnected. In this manner, the control module can be detached from the sensor module and connected to another sensor module. Thus, one control module can be used to measure more than one biosignal by using different sensor modules.

The control module comprises means for processing biosignal data sensed with the sensor module. These processing means can be used to convert the sensed biosignal data into a form which can be more easily forwarded or stored. The control module may, for example, comprise means for wirelessly transmitting processed biosignal data to a computing device, such as a PC, a tablet PC or a smart phone, for post-processing. The post-processing may, for example, be interpretation of the data and/or visualisation of the data on a user interface of the computing device.

For situations where no means for receiving the transmitted processed biosignal data are available, the control module may comprise a storage memory for storing processed biosignal data. The biosignal data may thus be gathered and stored to the storage memory and transferred later to a computing device for post-processing. The storage memory may, for example, be implemented as a non-volatile memory, such as a flash memory. The flash memory may be implemented in the form of a flash memory card, such as a Secure Digital (SD) card.

When the first connector and the first counterpart connector implement a standard computer interface, such as USB, the first counterpart connector of the control module can be connected to a computing device implementing the standard computer interface. Thus, the processed biosignal data can be transferred from the control module to the computing device through the standard computer interface. Further, the control module can be recharged through the computer interface.

The first counterpart connector can also be used for transferring data, such as parameters and configuration data, from the computing device to the control module.

The control module may comprise a rechargeable battery for providing operating power for the control module. The rechargeable battery allows wireless operation of the disclosed arrangement. The control module may also comprise means for supplying operating power for the sensor module through connection between the first connector and the first counterpart connector.

As the control module is detachable, the user is not bound to a charger charging the control module. If a second control module is available, the disclosed arrangement can be operated while a first control module is recharging. Electrodes for sensing the biosignal do not have to be removed while recharging. This allows use of permanent electrodes without restricting mobility of the user. As the biosignal data can be transferred and the control module can be recharged without having galvanic connection to the user, the personal safety of the user can be maintained.

The arrangement may further comprise means for producing audio feedback on the basis of the processed biosignal data. The disclosed arrangement may, for example, warn the user of heart overexertion or failure which can reduce the risk of a sudden cardiac arrest. The means for producing audio feedback may, for example, be implemented on the control module.

Figure 1B:
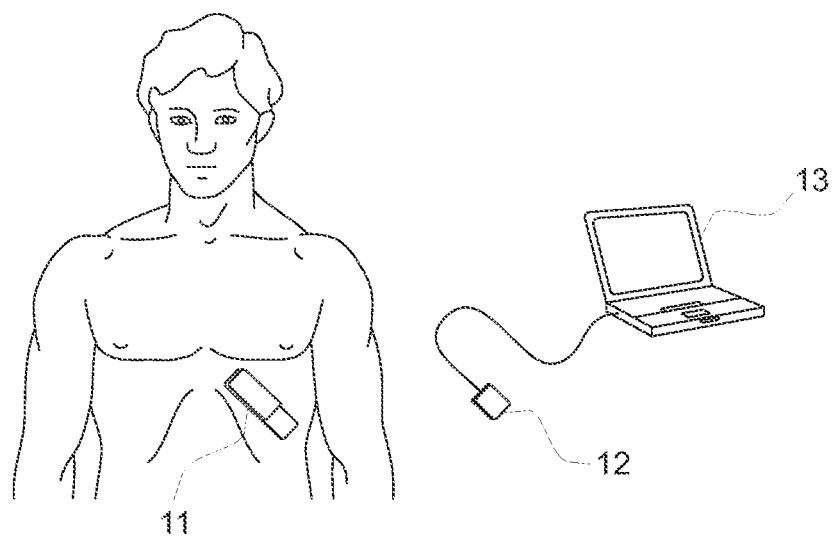

FIGS. 1a and 1b illustrate an exemplary embodiment of the disclosed arrangement for measuring a biosignal of a user wearing the arrangement. The arrangement comprises a sensor module 11 and a control module 12.

The sensor module 11 is connected to disposable electrodes attached to the chest of the user. The sensor module 11 may comprise measurement electronics, such as A/D conversion circuitry, which act as means for sensing heart rate variability (HRV). The sensor module 11 further comprises a micro-USB plug as the first connector for interfacing with the control module 12.

The control module 12 comprises a micro-USB receptacle as a first counterpart connector. The control module 12 also has a rechargeable battery for providing operating power for the control module. The control module 12 supplies operating power for the sensor module 11 through the micro-USB receptacle and plug. The micro-USB plug can be detached from the micro-USB receptacle, and the control module 12 can be attached to another sensor module or a computing device.

The control module 12 comprises means for processing biosignal data sensed with the sensor module. These means may, for example, be a microprocessor, a DSP, a FPGA or an ASIC. The means for processing may, for example, process the sensed biosignal data into a form suitable to be stored or transferred to a computing device.

For example, in FIGS. 1a and 1b, the control module 12 also has a Bluetooth chip as the means for wirelessly transmitting the processed biosignal data to a laptop PC 13. The PC 13 can then be used to post-process the biosignal data. For example, software operating on the PC 13 can be used to interpret the biosignal data, and information determined on the basis of the biosignal data can be shown on the screen of the PC 13. In FIG. 1a, the micro-USB receptacle of the control module 12 is connected to the micro-USB plug of the sensor module 11 and sends biosignal data wirelessly to the PC 13.

The control module 12 further comprises a storage memory for storing processed biosignal data implemented as an SD memory card. The size of the memory may, for example, be 2 to 32 GB. In FIG. 1b, the control module 12 has been detached from the sensor module 11 and attached to the PC 13 via a connector cable in order to transfer biosignal data to the PC and recharge the control module 12.

Figure 2:
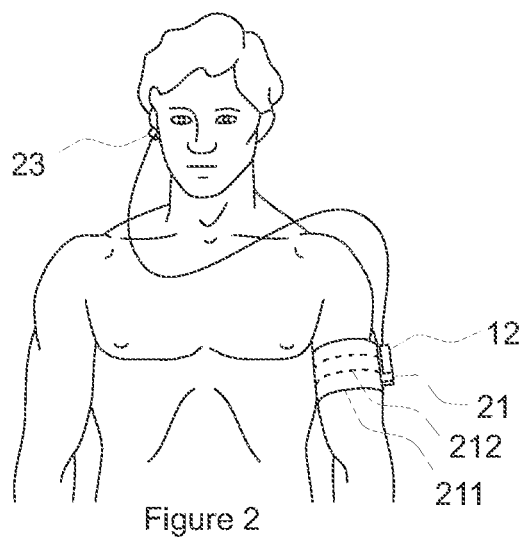
FIG. 2 illustrates another embodiment of the disclosed arrangement with an electrode adapted to be attached to the user's ear.

Under some conditions, electrode contacts to the body of the user in FIGS. 1a and 1b may be compromised by sweating and/or movement. Therefore, FIG. 2 illustrates another exemplary approach of the disclosed arrangement. The arrangement in FIG. 2 is also adapted for measuring heart rate variability (HRV) of a user wearing the arrangement. The arrangement comprises the control module 12 of FIGS. 1a and 1b and a sensor module 21. The sensor module 21 comprises an armband 211 comprising a first electrode 212 for sensing heart rate variability (HRV). The electrode 212 may, for example, be placed on the inside surface of the armband 211.

The sensor module 21 further comprises a micro-USB plug for interfacing with the control module 12. This allows the same control module as in FIGS. 1a and 1b to be used.

The arrangement of FIG. 2 further comprises a second electrode 23 for sensing heart rate variability (HRV), wherein the second electrode 23 is adapted to be attached to the user's ear. The second electrode 23 may further comprise means for sensing other biosignals, such as ear plethysmography. The control module 12 comprises a second connector for interfacing with the second electrode 23.

Alternatively, the second electrode may be adapted to be attached to the user's other arm. The second electrode may be in the form of another armband, for example. The control module 12 may be adapted to support both kinds of electrodes. Depending on the second electrode, the control module 12 may use different digital filtering and signal processing on the sensed biosignal.

Figure 4:
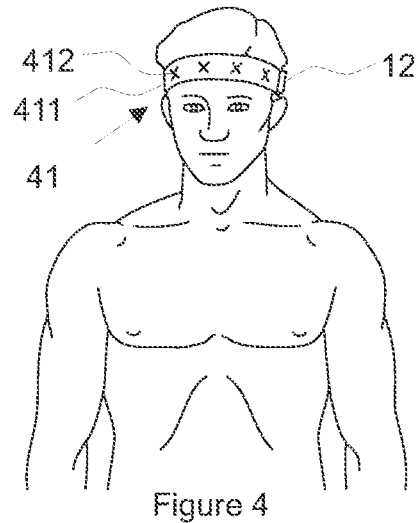
FIG. 4 illustrates yet another exemplary embodiment of the disclosed arrangement where the sensor module comprises a head band.
Figure 5:
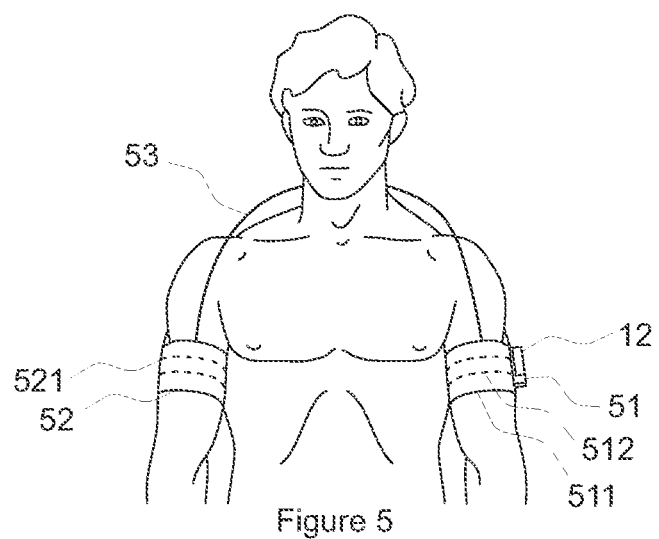
FIG. 5 illustrates an exemplary embodiment where a biosignal is measured between two arms.

FIG. 5 illustrates an exemplary embodiment where a biosignal is measured between the user's arms. The arrangement comprises a control module 12, which may be the same as in FIGS. 1a, 1b, 2, 3, and 4. The arrangement further comprises a sensor module 51. The sensor module 51 comprises a first armband 511 comprising a first electrode 512. The arrangement also comprises a second electrode 521 in a second armband 52. The electrodes 512 and 521 may be placed on the inside surfaces of the armbands 511 and 52, for example.

The second electrode 521 may be connected to the control module 12 through the second connector of the control module 12. Alternatively, the second electrode 521 may be connected to the control module 12 through the sensor module 51. FIG. 5 shows a connector cable 53 connecting the second electrode 521 to a connector on the first armband 511 of the sensor module 51. The sensor module 51 transmits the biosignal sensed with the first electrode 512 and second electrode 521 to the control module 12 through the first connector.

In FIG. 2, the second electrode 23 is connected to the second connector of the control module 12. In FIGS. 1a and 1b, the second connector of control module 12 is not used as the sensor module 11 already comprises two electrodes.

Figure 3:
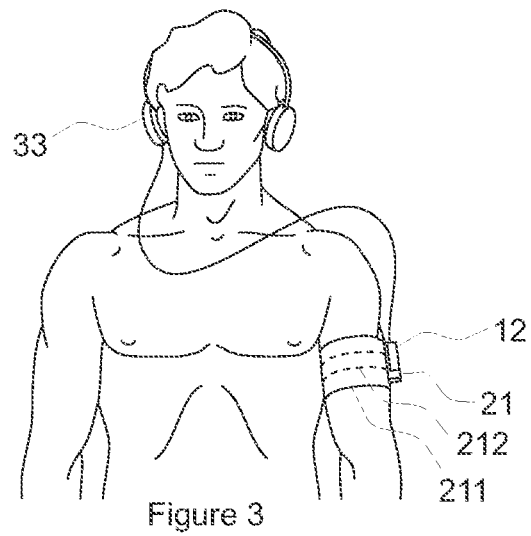
FIG. 3 illustrates yet another embodiment of the disclosed arrangement where an electrode is implemented in the form of headphones.

The second connector may be a standard headphone plug receptacle, and the second electrode may be implemented in the form of headphones. FIG. 3 illustrates an exemplary embodiment where the second electrode is implemented as headphones 33 adapted for forming a galvanic contact between the control module 12 and the user's ear.

In addition to sensing biosignals, the headphones 33 can be used as the means for producing audio feedback on the basis of the processed biosignal data. Through the headphones 33, the control module 12 can, for example, give, on the basis of the processed biosignal data, instructions and/or information to the user about suitable training intensity or performance levels.

In addition to the audio feedback responsive to the processed biosignal data, the control module may comprise an audio record player, such as an MP3 player. Audio records, for example music, may be stored in the storage memory used for storing the biosignal data and played back while measuring the biosignal.

FIG. 4 illustrates yet another exemplary embodiment of the disclosed arrangement. In FIG. 4, the sensor module 41 comprises a head band 411. The head band may comprise a plurality of electrodes 412 placed on the inside surface of the head band 411.

The arrangement of FIG. 4 with the head band 42 may, for example, be used for measuring eye movements and/or brain biosignals, such as alpha waves. The disclosed arrangement of FIG. 4 may, for example, be used to give an audio warning to a driver driving a car if the driver is about to fall asleep.

The control module 12 in FIGS. 1 to 4 may also comprise means for determining movements, position and/or activity of the user wearing the control module 12. These means can, for example, be implemented in the form of an accelerometer. The control module 12 may also comprise means for global positioning of the user. The means for global positioning may, for example, be implemented in the form of a GPS module in the control module 12.

It will be obvious to a person skilled in the art that the inventive concept can be implemented in various ways. The invention and its embodiments are not limited to the examples described above but may vary within the scope of the claims.

The invention claimed is:

1. A control module for measuring a biosignal, wherein the control module comprises:
   a first receptacle that attaches to a connector of a sensor module that has a first electrode that forms a galvanic contact to a user's skin and senses at least one biosignal;
   an audio record player;
   a second receptacle that that attaches to a connector of a second electrode that forms a galvanic contact to the user's skin and senses the at least one biosignal, wherein the second receptacle is configured to output an audio signal originating from the audio record player to the connector of the second electrode;
   means for processing the biosignal data sensed with the first electrode and the second electrode;
   a storage memory for storing processed biosignal data;
   a rechargeable battery that provides operating power for the control module; and
   means for wirelessly transmitting the processed biosignal data to a computing device, such as a PC, a tablet PC or a smart phone, for post-processing;
   wherein the control module is configured to sense the at least one biosignal by having a galvanic connection to the first electrode through the first receptacle while at the same time having a galvanic connection to the second electrode through the second receptacle.

2. A control module as claimed in claim 1, wherein the control module is configured to measure an electrical biosignal that is obtained in a measurement arrangement where the second electrode is configured to be attached to the user's ear.

3. A control module as claimed in claim 1, wherein the control module is configured to measure an electrical biosignal that is obtained in a measurement arrangement where the second electrode is configured to be attached to the user's arm.

4. A control module as claimed in claim 1, wherein the control module comprises:
   means for supplying operating power for the sensor module through connection between the connector of the sensor module and the first receptacle.

5. A control module as recited in claim 1, in which the audio signal output by the second receptacle is audio feedback based on the sensed biosignal data.

6. An arrangement for measuring a biosignal, wherein the arrangement comprises the control module as claimed in claim 1, and a sensor module comprising:
   a first electrode that forms a galvanic contact to the user's skin; and
   a connector that attaches to the first receptacle of the control module in order to sense at least one biosignal with the aid of a second electrode.

7. An arrangement as claimed in claim 6, wherein the first connector of the sensor module and the first receptacle implement a USB interface.

8. An arrangement as claimed in claim 6, wherein the arrangement comprises:
   means for producing audio feedback on the basis of the processed biosignal data.

9. An arrangement as claimed in claim 6, wherein:
the arrangement is configured to measure heart rate variability of a user wearing the arrangement,
the sensor module comprises an armband comprising the first electrode for sensing heart rate variability (HRV), and
the arrangement further comprises a second electrode for sensing heart rate variability (HRV), wherein the second electrode comprises a connector that is connected to the second receptacle of the control module and wherein the second electrode is configured to be attached to the user's ear.

10. An arrangement as claimed in claim 6, wherein the second electrode is adapted to be attached to the user's ear.

11. An arrangement as claimed in claim 10, wherein the second electrode further comprises means for ear plethysmography.

12. An arrangement as claimed in claim 9, wherein:
the second electrode is implemented as a headphone set configured to form a galvanic contact between the control module and the user's ear.

13. An arrangement as claimed in claim 6, wherein the arrangement further comprises a second electrode that is configured to be attached to the user's arm.

14. An arrangement as claimed in claim 6, wherein the sensor module comprises a head band comprising a plurality of electrodes.

15. An apparatus for measuring a biosignal, the apparatus comprising:
a sensor module that has:
a first electrode forming a galvanic contact to a user's skin and sensing at least one biosignal; and
a connector that is connected to the first electrode; and
a control module that has:
an audio record player;
means for processing sensed biosignal data;
a storage memory for storing processed biosignal data;
a rechargeable battery that provides operating power for the control module;
means for wirelessly transmitting the processed biosignal data to a computing device, such as a PC, a tablet PC or a smart phone, for post-processing;
a first receptacle that attaches to the connector of the sensor module; and
a second receptacle that attaches to the connector of a second electrode forming a galvanic contact to the user's skin and sensing the at least one biosignal,
wherein the second receptacle is configured to output an audio signal originating from the audio record player to the connector of the second electrode, and the control module is configured to sense the at least one biosignal by having a galvanic connection to the first electrode through the first receptacle while at the same time having a galvanic connection to the second electrode through the second receptacle.

16. A control module for measuring a biosignal, wherein the control module comprises:
a first receptacle that detachably attaches to a connector of a sensor module that has a first electrode that forms galvanic contact to the user's skin and senses at least one biosignal;
a second receptacle that detachably attaches to a connector of a second electrode that forms a galvanic contact to the user's skin and senses the at least one biosignal;
means for processing biosignal data sensed with the first electrode and the second electrode;
a storage memory in which processed biosignal data is stored;
a rechargeable battery that provides operating power for the control module; and
means for wirelessly transmitting the processed biosignal data to a computing device, such as a PC, a table PC or a smart phone, for post-processing,
wherein the control module is configured to measure the at least one biosignal in a measurement arrangement where the second electrode is attached to the user's ear, and to sense the at least one biosignal by having a galvanic connection to the first electrode through the first receptacle while at the same time having a galvanic connection to the second electrode through the second receptacle.

17. A control module as recited in claim 16, in which the control module creates audio feedback based on the sensed biosignal data and outputs that audio feedback through the second receptacle.

* * * * *